(12) United States Patent
Park et al.

(10) Patent No.: US 10,359,344 B2
(45) Date of Patent: Jul. 23, 2019

(54) COMPOSITION FOR CLEARING OF BIOTISSUE AND CLARITY METHOD FOR BIOTISSUE USING THEREOF

(71) Applicant: KOREA RESEARCH INSTITUTE OF CHEMICAL TECHNOLOGY, Daejeon (KR)

(72) Inventors: SunHyun Park, Daejeon (KR); Ki-Suk Kim, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 65 days.

(21) Appl. No.: 15/622,529

(22) Filed: Jun. 14, 2017

(65) Prior Publication Data
US 2018/0306687 A1    Oct. 25, 2018

(51) Int. Cl.
*G01N 1/34*    (2006.01)
*G01N 1/30*    (2006.01)
*C07J 41/00*    (2006.01)

(52) U.S. Cl.
CPC ............ *G01N 1/30* (2013.01); *C07J 41/0061* (2013.01); *G01N 1/34* (2013.01); *G01N 2001/305* (2013.01)

(58) Field of Classification Search
CPC .................................................... A61K 31/575
USPC .................................................. 514/182, 588
See application file for complete search history.

(56) References Cited

U.S. PATENT DOCUMENTS

| 8,198,245 B2 * | 6/2012 | Niklason | A61K 8/64 514/18.8 |
| 2014/0199686 A1 * | 7/2014 | Liu | C12N 1/06 435/5 |
| 2017/0227430 A1 * | 8/2017 | Marini | G01N 1/30 |

FOREIGN PATENT DOCUMENTS

| JP | 2003-066035 | 3/2003 |
| JP | 2015-049101 | 3/2015 |
| WO | WO 2011/111876 A1 | 9/2011 |
| WO | WO 2016/023009 A1 | 2/2016 |
| WO | WO 2016/147812 A1 | 9/2016 |

OTHER PUBLICATIONS

Richardson et al. "Clarifying Tissue Clearing," Cell. 2015, vol. 162, No. 2, pp. 246-257 (Year: 2015).*

(Continued)

*Primary Examiner* — Shengjun Wang
(74) *Attorney, Agent, or Firm* — Klarquist Sparkman, LLP (57) ABSTRACT

The present invention relates to a composition for clearing biotissue and a clarity method for biotissue using the same. The composition for clearing biotissue and the clarity method for biotissue using the same of the present invention do not need a high price electrophoresis apparatus and expensive solutions, and can not only be applied to various biotissues including brain, liver, lung, kidney, intestine, heart, muscle, and blood vessel, without damaging any of them but also prevent bubble formation, color change, and dark sediment; improve the clarity of biotissues; and help antibody-staining of the cleared tissues. Therefore, it is useful to identify the reason of various diseases through structural imaging of biotissue and to establish a treatment method.

8 Claims, 10 Drawing Sheets

(56) References Cited

OTHER PUBLICATIONS

Kuno et al., "One-cell resolution three-dimensional anatomy/pathology at organ in individual scale," *Kagakutoseibutu* (*Japan*) 53(11): 737-740 (2015)(English translation of the legend of Fig. 4 is provided).
Susaki et al., "Whole-brain imaging with single-cell resolution using chemical cocktails and computational analysis," *Cell* 157: 726-736 (Apr. 24, 2014).

* cited by examiner

COMPOSITION FOR CLEARING OF BIOTISSUE AND CLARITY METHOD FOR BIOTISSUE USING THEREOF

This application claims priority to KR Patent Application No. 10-2017-0051443 filed on Apr. 21, 2017. The disclosure of that prior filed application is incorporated herein by reference.

BACKGROUND OF THE INVENTION

1. Field of the Invention

The present invention relates to a composition for clearing biotissue and a clarity method for biotissue using the same.

2. Description of the Related Art

Medical diagnostic technology using x-ray has been developed as a technology capable of three-dimensional observation and elaborate diagnosis by two-dimensional scanning such as CT or MRI. Another technique to realize a three dimensional image using ultrasound instead of a light source is also used for diagnosis. However, most techniques developed so far have the macro-resolution of millimeter level. The three-dimensional measurement techniques at micro-level that can realize the analysis at cellular level have not been fully established. Thus, moat of cell analysis methods use the conventional two dimensional techniques.

That is, in order to analyze the microstructure, a biotissue such as a biopsy tissue or an autopsy tissue is fixed in a fixing solution, and embedded in paraffin or polymer; the sample is made into sections in the thickness of micrometers or nanometers so as to let light or electronic wave pass through; and then transmission Images are observed by optical or electron microscope.

To obtain a three dimensional mage using the micro-imaging technique, a confocal microscope is needed. With this, thickness information of tens of micrometers can be obtained. The thickness is limited by the depth at which the light source can penetrate. However, since most of the structures in living tissues have size of several hundreds of micrometers or more, only a part of the potential information can be obtained using the method above. Therefore, in order to obtain a thicker tissue image, a series of sections in the thickness of tens of micrometers are prepared, followed by imaging of each by using a microscope. Then, the image has to be reconstructed. In particular, when imaging a whole neuron of the brain tissue, since one neuron can stretch its axon up to a few meters, a series of processes wherein the tissue has to be cut and attached again is necessary, during which the problems that can occur are numberless.

With the tissue clarity method, the internal structure and protein distribution in the tissue can be observed without tissue damage. The advanced method today can overcome the limit of the conventional technique and facilitate the observation of the deep inside of the structure and give more information about the integral structure with various systems and molecular information, which encourages the development of the clarity method for tissue with different angles.

As for the conventional tissue clarity method, Spatleholz, BABB, Scale S, and iDISCO using an organic solvent, and ACT (active clarity technology) using a polymer to maintain the antigen conservation in the treated tissue have been reported. Except ACT, all other methods display the decrease of fluorescence and antigen conservation. In the case of ACT, the antigen conservation reaches at least 90%, which is much higher than other methods using a hydrogel polymer binding to the fixed protein. However, such a strong tissue binding process can cause the loss of antigenicity, resulting in the decrease of valuable antibodies. Therefore, the conventional methods need to be improved.

The 'CLARITY' based technique which was developed recently for tissue clarity, uses a net supporter which is constructed in a tissue to hold materials important for diagnosis such as DNA or proteins by using hydrogel and eliminates lipids selectively (see non-patent reference 1).

However, according to the method above, the hydrogel supporter invades into a tissue. When the concentration of hydrogel is increased, the binding with a protein is increased and the net structure gets tighter, meaning the tissue becomes harder. Once the tissue gets harder, it is hard for the lipid to escape by using a surfactant, indicating time for the clarity process takes longer. Besides, the method above has other disadvantages such as air and dark particles being deposited on the tissue surface, making yellow tissues.

The method above also requires many additional apparatuses and the process is very complicated. For example, in order to clear brain alone, it costs over 30,000,000 Korean Won. This method can clear one at a time, meaning if it tries to clear the brain, it can only clear the brain alone, indicating the method is not economical and can be time-consuming. The bigger problem is that an antibody staining material is hard to pass through the polyacrylamide net structure.

To obtain the protein distribution information in tissue, it is necessary to increase the physical diffusion of an antibody, considering antigen conservation and antibody permeability. However, if the tissues are hard and have many connective tissues, the diffusion rate of an antibody would be decreased significantly. So, a new technology to overcome the problems above is required.

As explained above, the conventional technique is not only complicated but also costly and time-consuming for tissue clarity. Therefore, it is required to develop a new technique to clear various tissues including brain tissues by optimizing the process, expense, and antibody staining.

The present inventors developed a technique for clearing biotissue. In the course of the study, the present inventors confirmed that the composition for clearing biotissue and the clarity method for biotissue using the same of the present invention do not need a high price electrophoresis apparatus and expensive solutions, and can not only be applied to various biotissues including brain, liver, lung, kidney, intestine, heart, muscle, and blood vessel, without damaging any of them but also prevent bubble formation, color change, and dark sediment; improve the clarity of biotissues; and help antibody-staining of the cleared tissues, so that the composition and the method can be effectively used to identify a reason of various diseases by the obtained structural images of biotissue and to establish a treatment method of disease, leading to the completion of the present invention.

PATENT REFERENCE

International Patent Publication No. WO 2016/108359

NON-PATENT REFERENCE

Chung K, et al. (2013) Nature 497(7449):332-337.
Lee H, et al. BMC Developmental Biology 2014 14:781.

SUMMARY OF THE INVENTION

It is an object of the present invention to provide a composition for clearing biotissue.

It is another object of the present invention to provide a clarity method for biotissue.

Figure 2:
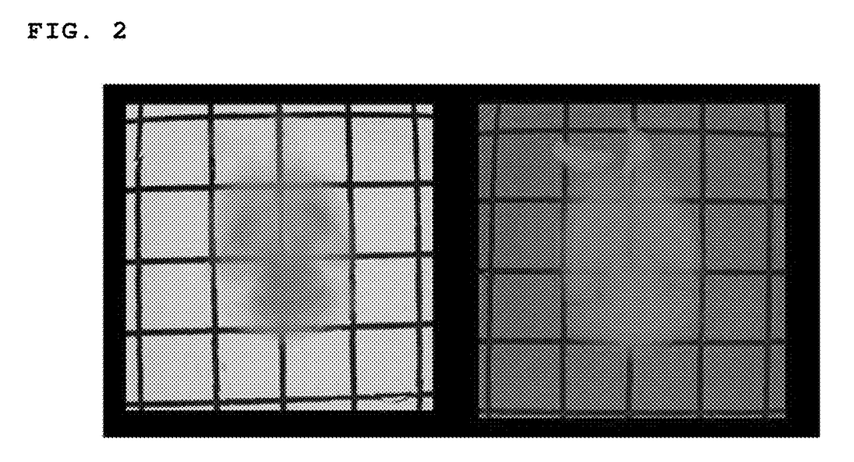
FIG. 2 is an image of the total mouse brain completely cleared by the clarity method for tissue of the invention.

To achieve the above objects, the present invention provides a composition for clearing biotissue comprising the compound represented by formula 1 below, the optical isomer, the hydrate, or the salt of the same.

wherein the fluorescence of Glutamic Acid Decarboxylase67-GFP (GAD 67-GFP) is shown in the brain via ultraviolet (UV).

Figure 3:
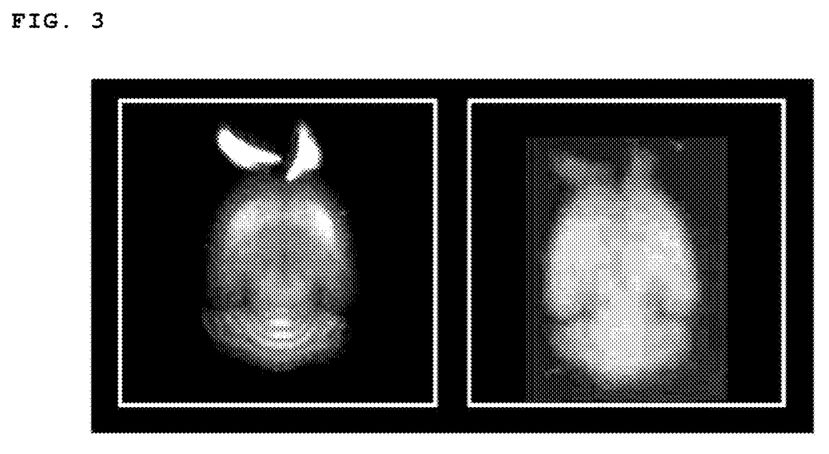
Figure 4:
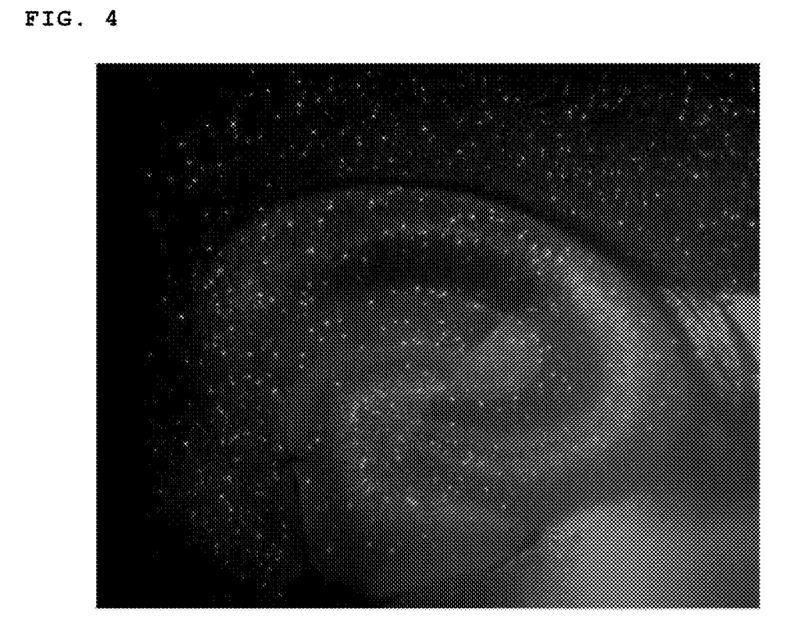
FIGS. 4-7 are images showing the immunostaining and GFP signal investigated by MicroscopyLightsheet Z.1 using 5× and 20× objective lens.
Figure 5:
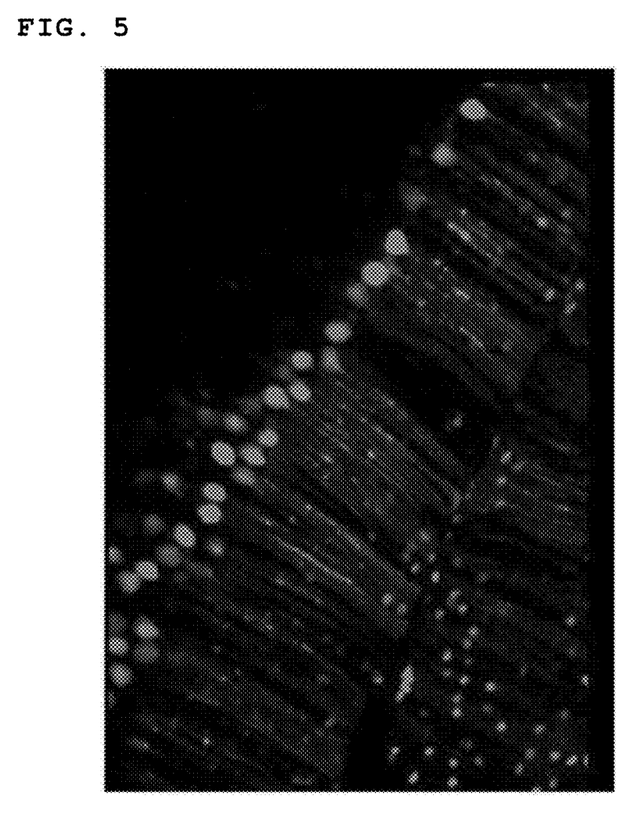
Figure 6:
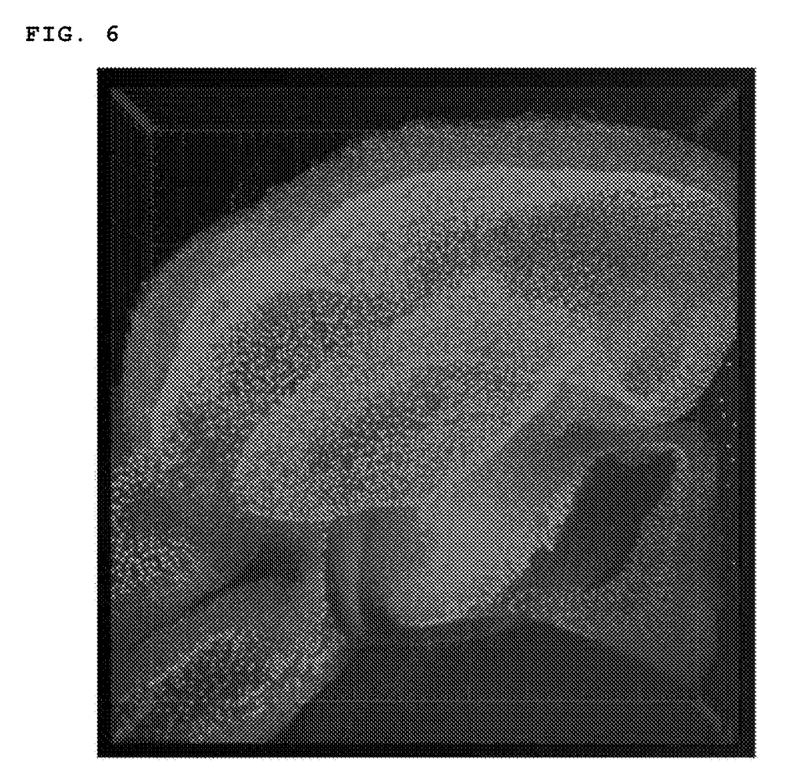

FIG. 3 is an image showing the fluorescence of GAD67-GFP and Alexa fluor-647 observed in the clarified brain after the treatment of choline acetyltrasnferase antibody.

[Formula 1]

In the formula 1, $R^1$ and $R^2$ are independently $C_{1-10}$ straight or branched alkyl; and p, q and r are independently integers of 0~10.

In addition, the present invention provides a clarity method for biotissue comprising the step of clearing the fixed biotissue by contacting the fixed tissue with the composition of the invention.

Advantageous Effect

The composition for clearing biotissue and the clarity method for biotissue using the same of the present invention do not need a high price electrophoresis apparatus and expensive solutions, and can not only be applied to various biotissues including brain, liver, lung, kidney, intestine, heart, muscle, and blood vessel, without damaging any of them but also prevent bubble formation, color change, and dark sediment; improve the clarity of biotissues; and help antibody-staining of the cleared tissues, so that the composition and the method can be effectively used to identify a reason of various diseases by the obtained structural images of biotissue and to establish a treatment method of disease.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Hereinafter, the present invention is described in detail.

The present invention provides a composition for clearing biotissue comprising the compound represented by formula 1 below, the optical isomer, the hydrate, or the salt of the same.

[Formula 1]

In the formula 1, $R^1$ and $R^2$ are independently $C_{1-10}$ straight or branched alkyl; and p, q and r are independently integers of 0~10.

Preferably, $R^1$ and $R^2$ are independently $C_{1-5}$ straight or branched alkyl; and p, q and r are independently integers of 0~5.

More preferably, $R^1$ and $R^2$ are methyl; and p, q and r are the integer 1.

Most preferably, the compound represented by formula 1 is the compound represented by formula 2 below or the hydrate thereof.

[Formula 2]

Hereinafter, the composition for clearing biotissue of the invention is described in more detail.

The composition for clearing biotissue of the present invention removes the lipid component that blocks transmission of light and other molecules from the biotissue, does not cause structural degeneration of the protein, and serves to tighten the tissue.

In the composition for clearing biotissue of the invention, the concentration of the compound represented by formula 1 is preferably 2-55 w/v % (weight/volume %) and more preferably 4-50 w/v %. At this time, as the solution showing the concentration, simulated body fluid used in ordinary fields can be used, which is more precisely exemplified by distilled water, PBS (phosphate buffer saline), and TBS (tris buffer solution), but not always limited thereto.

If the concentration of the compound represented by formula 1 is less than 2 w/v %, the clarity speed of biotissue would be lowered significantly. If the concentration of the compound is higher than 55 w/v %, CHAPS represented by formula 1 would not be dissolved completely.

Further, the composition for clearing biotissue of the invention can additionally include a substance that can accelerate biotissue clearing by controlling osmotic pressure. At this time, the substance that can accelerate biotissue clearing is selected from the group consisting of urea, CHAPSO (3-([3-Cholamidopropyl]dimethylammonio)-2-hydroxy-1-propanesulfonate), sucrose, fructose, glycerol, diatrizoic acid, Triton X-100, Tween-20, 2,2'-thiodiethanol, iohexol, chloral hydrate, and a combination thereof, but not always limited thereto.

The concentration of the substance that can accelerate biotissue clearing is preferably 5-80 w/v %, 5-75 w/v %, 10-70 w/v %, 5-50 w/v %, or 35-60 w/v %. If the concentration is less than 5 w/v %, the speed of biotissue clearing is too slow. If the concentration is higher than 80 w/v %, crystals would be formed or solubility would be very poor. In a preferred embodiment of the present invention, as the substance that can accelerate biotissue clearing, urea was used. At this time, the concentration of urea was 10-70 w/v % and more preferably 20-60 w/v %. The concentration of the substance that can accelerate biotissue clearing can be regulated properly along with the concentration of the compound represented by formula 1.

According to the conventional clarity method, a mounting solution has to be additionally purchased or prepared to adjust refractive index of the tissue and solution. However, the composition for clearing biotissue of the present invention does not require the solution to adjust refractive index, which saves production costs. Also, the conventional clarity method causes the tissue to swell, but the composition of the present invention does not cause any size changes of the tissue.

As explained hereinbefore, the composition for clearing biotissue of the invention does not require a high price electrophoresis apparatus and expensive solutions; can be applied to various biotissues such as brain, liver, lung, kidney, intestine, heart, muscle, and blood vessels, without damaging any of those tissues; does not cause bubble formation, color change, or dark sediment; and can improve clarity of biotissue, so that it can be effectively used as a composition for clearing biotissue.

The present invention also provides a clarity method for biotissue comprising the step of clearing the fixed biotissue by contacting the fixed tissue with the composition above.

Hereinafter, the clarity method for biotissue of the invention is described in more detail.

The clarity method for biotissue of the present invention contains the step of clearing the fixed biotissue by contacting the fixed tissue with the composition above.

Particularly, the clarity method for biotissue of the invention is characterized by making the light invade more deeply by making the biotissue clearer by changing the physiochemical characteristics of the biotissue by contacting the tissue with the compound represented by formula 1.

The clarity method for biotissue of the invention does not cause bubble formation, color change, and dark sediment, either, and instead improves clarity of biotissue without losing or distorting the information of the tissue by protein degeneration. In particular, it is helpful to use various fluorophores including GFP protein to obtain useful information of tissue.

In the clarity method for biotissue of the present invention, the biotissue is not limited as long as it does not lose antigenicity before clarification and can be fixed.

More particularly, the fixation of biotissue can be performed by the conventional method using paraformaldehyde, ethylene glycol diglycidyl ether, dipropylene glycol diglycidyl ether, 1,4-butanediol diglycidyl ether, glycerol polyglycidyl ether, glutaraldehyde, polyacrylamide, or a combination thereof, but not always limited thereto.

In a preferred embodiment of the present invention, treatment of CHAPS and urea mixture increased the structural cohesion of protein, did not cause denaturation, made the tissue harder, prevented tissue swelling in the process of tissue clearing, and prevented from cracking in the process of washing. As the solution showing the concentration, simulated body fluid used in ordinary fields can be used, which is more precisely exemplified by distilled water, PBS (phosphate buffer saline), and TBS (tris buffer solution), but not always limited thereto. The impregnation can be performed at 10° C.-50° C., 12-48° C., 14-46° C., 16-44° C., 18-42° C., 20-40° C., 24-39° C., 28° C.-38° C., 30° C.-37° C., or 33-34° C.

The clarity method for biotissue of the present invention can be applied to various vertebrate tissues, particularly to brain, blood vessel, liver, lung, kidney, pancreas, and intestine, and is useful for the clarification of whole biotissue at once.

Further, the present invention provides a method for detecting important information in the cleared tissue such as DNA, RNA, protein, and fluorescent signal, etc.

Protein or mRNA in the biotissue cleared by the method of the invention can be detected by GFP fluorescence or immunostaining. When the protein is fixed, during the fixing process, the amino groups are linked together to form a network, which gives stability. In the meantime, nucleic acid such as RNA or DNA does not have amino groups, indicating it is comparatively unstable in the fixed tissue. In particular, in the course of electrophoresis, the position thereof can be changed in the tissue due to the electric characteristics of the nucleic acid. On the other hand, the biotissue cleared by the method of the invention is excellent in fluorescence staining for GFP cells and Choline Acetyltransferase, the cholinergic neuron marker antibody.

The clarity method for biotissue of the present invention can give the image enabling the three-dimensional observation of the undamaged biotissue cell and molecule distribution. So, observation studies can be carried out with a complete structure of several hundred micrometers or more for various biotissues with complicated structures. Thus, this method can be effectively used to identify the causes of various diseases including brain disease by gathering necessary information from the tissue.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Experimental Example 1: Confirmation of Clarity of Biotissue

To investigate whether or not the composition for clearing biotissue of the present invention could easily clarify biotissues, the following experiment was performed. All the animal tests described in this statement were performed according to the guidance (Approval No. RS17003) of Committee for Animal Resources, Korea Institute of Toxicology.

Particularly, adult mice (8 weeks old) were anesthetized with Isoflurane (1 cc/min), an inhalation anesthetic. To stain the mouse blood vessels, Lectin-488 (Cat# DL1174) was injected through the tail vein. 5 minutes after the injection, 50 mL of ice cold 1×PBS was perfused, and then ice cold PBS containing 4% PFA was perfused again. Organs were extracted and dipped in 4% paraformaldehyde and PFA solution, followed by incubation at 4° C. for 12 hours. At this time, the temperature for ice cold condition is not limited but preferably −20° C. to 40° C.

Next, the sample was washed with 50 ml of PBS twice. The fixed sample was incubated in PBS containing CHAPS (20 w/v %) and urea (60 w/v %) at 37° C. at 220 rpm for 3 days. The results are shown in FIG. 1.

The brain sample was transferred from the CHAPS and urea mixture into third distilled water. The sample was washed with 50 ml of third distilled water three times for 12 hours. The brain was transferred again into the mounting solution, the CHAPS and urea mixture, and clarity of the brain was observed. The results are shown in FIG. 2.

Figure 1:
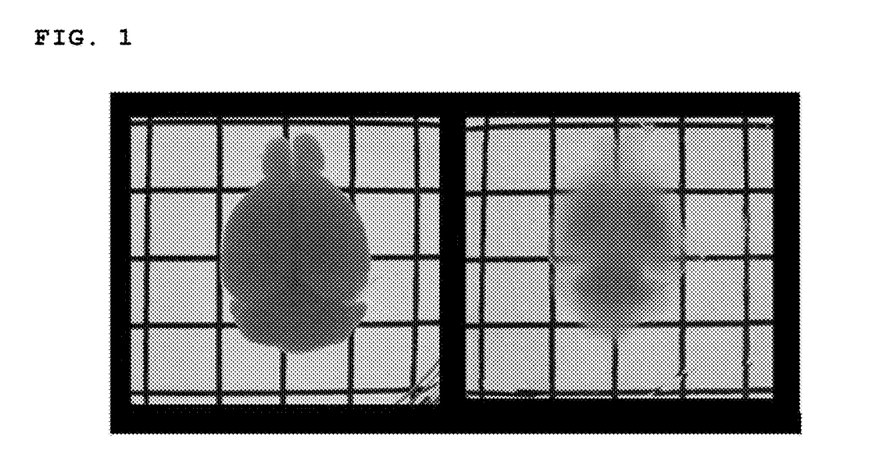
FIG. 1 is an image of the mouse brain which is under the clarity process according to the clarity method for tissue of the invention.

As shown in FIG. 1 and FIG. 2, the composition for clearing biotissue of the present invention was efficient in clearing biotissue.

Experimental Example 2: Observation of Fluorescence Images of GFP and Alexa Fluor-594 in the Clarified Adult Mouse Brain To observe fluorescence in the brain clarified by the method of the invention, immunostaining fluorescence and green fluorescent protein (GFP) signal were observed in the mouse brain by using an optical microscope (Leica) with 1× objective lens.

Figure 7:
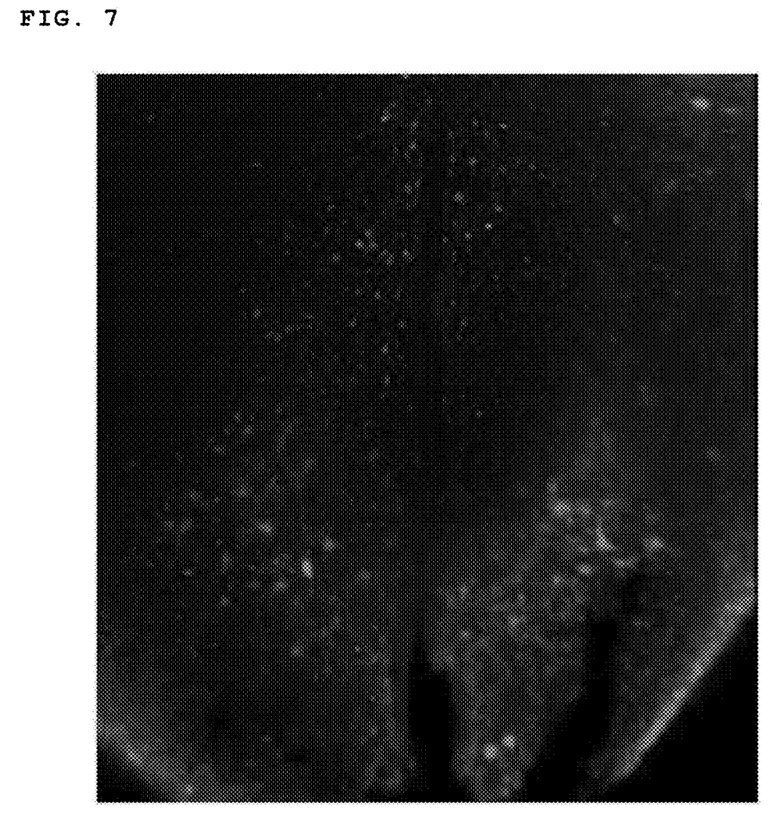
Figure 8:
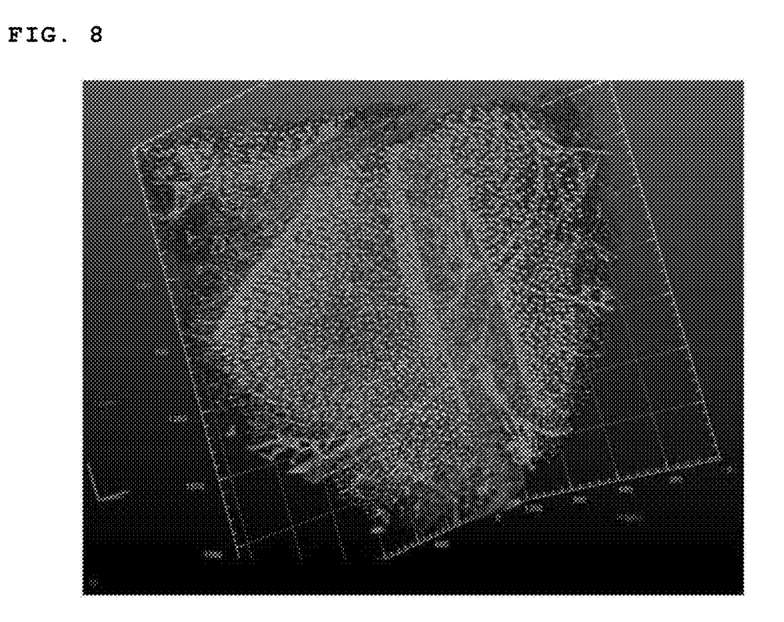
FIG. 8 is an image showing the fluorescence of GAD67-GFP and Alexa fluore-647 after the treatment of tyrosine-hydroxylase antibody.

Particularly, the tissue clarified in Experimental Example 1 was incubated for 12 hours, during which the sample was washed with 50 ml of distilled water three times. Then, the sample was loaded in the mixed solution comprising Choline Acetyltransferase (Cat# ab34419), the cholinergic neuron marker antibody (FIG. 3), Tyrosine Hydroxylase (Cat# ab112), the dopaminergic neuron marker antibody (FIG. 8), 0.1% Triton X-100, and 0.1% PBS, followed by incubation at 4° C. for 3 days. Three days later, the sample was washed with distilled water for 12 hours, followed by incubation with the secondary antibody Lectin-594 (FIG. 7), donkey anti-chicken IgG Alexa Fluor-647 (FIGS. 3-8), or donkey anti-rabbit IgG Alexa Fluore-647 (FIG. 8) for 3 days at 4° C. The sample was washed with 1×PBS for 6 hours. After washing, the sample was loaded in the mounting solution comprising CHAPS and urea, followed by incubation for 12 hours. Then, fluorescence was observed with an optical microscope. The results are shown in FIG. 3.

As shown in FIG. 3, fluorescence images were well observed in the brain clarified by the clarity method of the invention.

As shown in FIGS. 4-8, immunostaining images and GFP signals were observed by using MicroscopyLightSheet Z.1 with 5× and 20× objective lens. Three-dimensional images were reconstructed by using Zeiss software. Therefore, it was confirmed that the clarity method for biotissue of the present invention can apply to blood system, degenerative brain disease, and various other diseases. It can be confirmed that the tissue (cell) is transparent.

Figure 9:
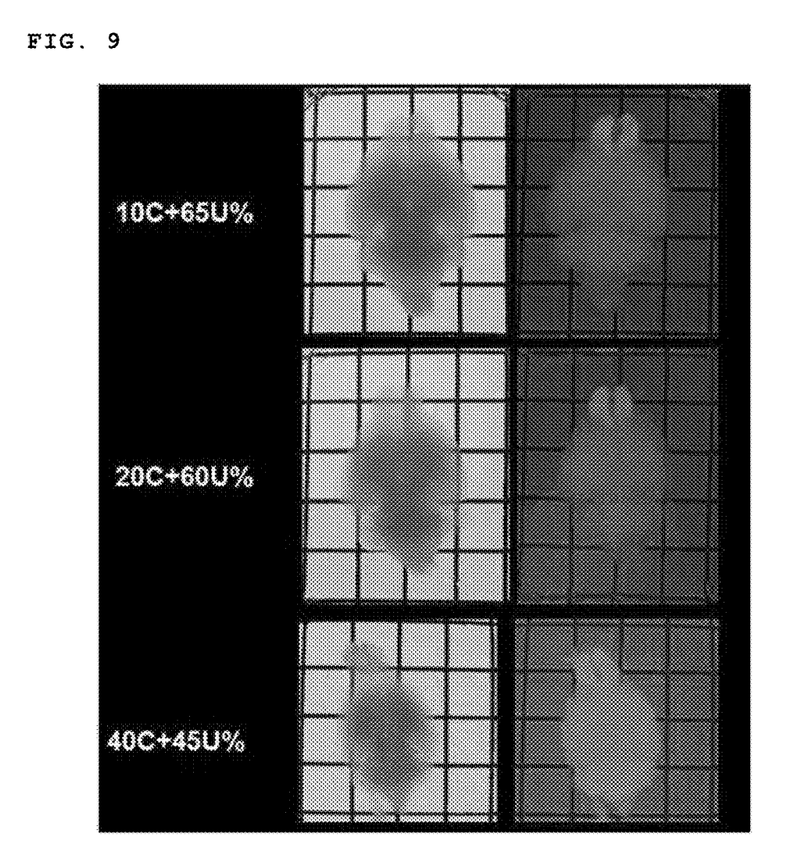
FIG. 9 is an image showing the CHAPS concentration dependent fluorescence strength and the sample sizes.

FIG. 9 is an image showing the CHAPS concentration dependent fluorescence strength and the sample sizes. It can be confirmed that the tissue (cell) is transparent.

Figure 10:
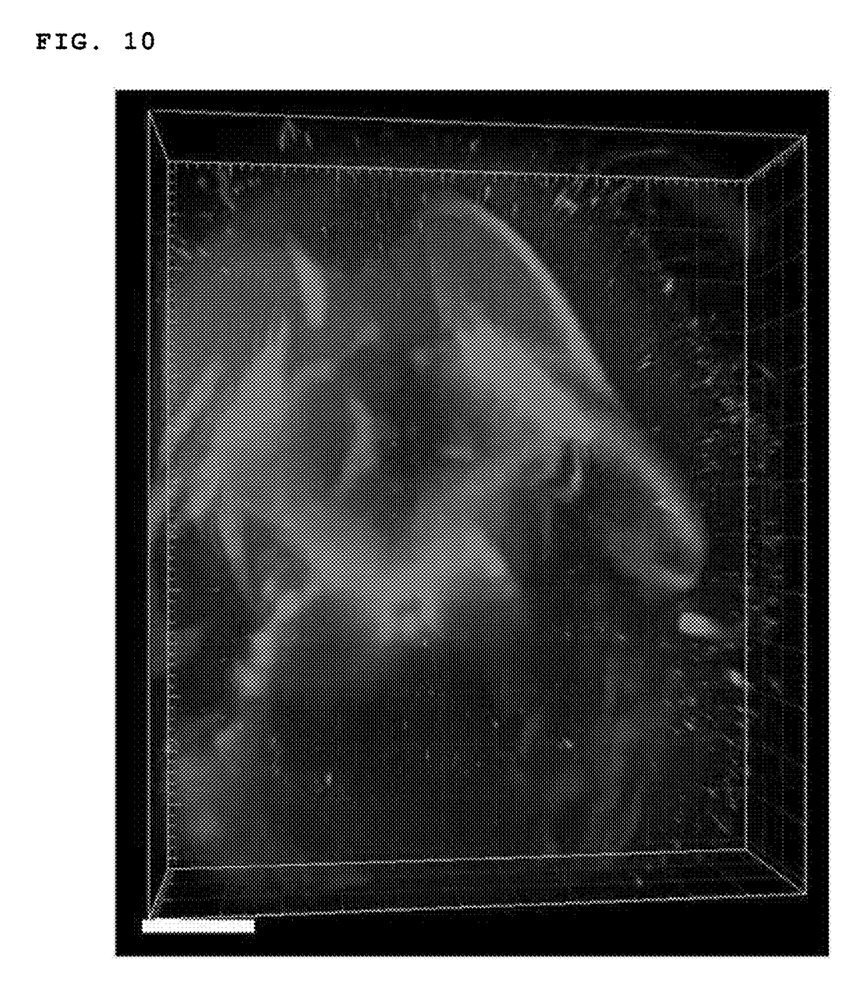
FIG. 10 is an image showing the fluorescence of GAD67-GFP and Donkey Anti-rabbit IgG Alexa Fluor-647 in Th-ab.

FIG. 10 is an image showing the fluorescence of GAD67-GFP and Donkey Anti-rabbit IgG Alexa Fluor-647 in Th-ab. It can be confirmed that the tissue (cell) is transparent.

What is claimed is:

1. A method for clarifying biotissue comprising the clearing fixed biotissue, comprising
   contacting the fixed biotissue with a composition, wherein the composition comprises about 2-55% weight (w)/volume (v) % of a compound represented by formula 2 below, or the hydrate thereof

[Formula 2]

and about 10-70 w/v % of urea;

thereby clarifying the biotissue.

2. The method for clarifying biotissue according to claim 1, wherein the fixed biotissue is fixed by one or more materials selected from the group consisting of paraformaldehyde, ethylene glycol diglycidyl ether, dipropylene glycol diglycidyl ether, 1,4-butanediol diglycidyl ether, glycerol polyglycidyl ether, glutaraldehyde and polyacrylamide.

3. The method for clarifying biotissue according to claim 1, wherein fixed biotissue is contacted with the composition at the temperature between 4° C.-50° C. and wherein the composition comprises about 4-50 w/v % of the compound represented by formula 2 and about 20-60 w/v % urea.

4. The method for clarifying biotissue according to claim 1, wherein the biotissue is brain, blood vessel, liver, lung, kidney, pancreas, or intestinal tissue.

5. The method for clarifying biotissue according to claim 3, wherein the compositions comprises about 4-50 w/v % of the compound represented by formula 2 and about 35-60 w/v % of urea.

6. The method for clarifying biotissue according to claim 1, wherein the compositions comprises about 20 w/v % of the compound represented by formula 2 and about 60 w/v % of urea.

7. The method for clarifying biotissue according to claim 1, wherein the compositions comprises about 10 w/v % of the compound represented by formula 2 and about 65 w/v % of urea.

8. The method for clarifying biotissue according to claim 1, wherein the compositions comprises about 40 w/v % of the compound represented by formula 2 and about 45 w/v % of urea.

* * * * *